US009402812B2

(12) United States Patent
Javeri et al.

(10) Patent No.: US 9,402,812 B2
(45) Date of Patent: Aug. 2, 2016

(54) METHODS FOR THE PREPARATION OF LIPOSOMES

(75) Inventors: Indu Javeri, Andover, MA (US); Kaliappanadar Nellaiappan, Lexington, MA (US); Bharat Dixit, Braintree, MA (US)

(73) Assignee: Indu Javeri, Andover, MA (US)

( * ) Notice: Subject to any disclaimer, the term of this patent is extended or adjusted under 35 U.S.C. 154(b) by 0 days.

(21) Appl. No.: 12/889,248

(22) Filed: Sep. 23, 2010

(65) Prior Publication Data

US 2011/0070292 A1    Mar. 24, 2011

Related U.S. Application Data

(60) Provisional application No. 61/245,185, filed on Sep. 23, 2009.

(51) Int. Cl.
*A61K 9/127* (2006.01)
*A61K 31/337* (2006.01)
*A61K 9/00* (2006.01)
*A61K 9/19* (2006.01)

(52) U.S. Cl.
CPC ............... *A61K 9/127* (2013.01); *A61K 9/1278* (2013.01); *A61K 31/337* (2013.01); *A61K 9/0095* (2013.01); *A61K 9/19* (2013.01)

(58) Field of Classification Search
CPC ...................................................... A61K 9/127
USPC ......................................................... 424/450
See application file for complete search history.

(56) References Cited

U.S. PATENT DOCUMENTS

| | | | |
|---|---|---|---|
| 3,581,088 A | | 5/1971 | Engels |
| 4,291,024 A * | | 9/1981 | Turcotte ...................... 536/26.2 |
| 4,356,167 A * | | 10/1982 | Kelly ............................ 424/450 |
| 4,508,703 A | | 4/1985 | Redziniak et al. |
| 4,814,270 A | | 3/1989 | Piran |
| 4,857,319 A | | 8/1989 | Crowe et al. |
| 4,880,635 A * | | 11/1989 | Janoff et al. ................... 424/450 |
| 4,895,452 A * | | 1/1990 | Yiournas et al. ........... 366/165.1 |
| 4,911,928 A | | 3/1990 | Wallach |
| 4,970,076 A | | 11/1990 | Horrobin |
| 5,204,112 A * | | 4/1993 | Hope et al. .................... 424/450 |
| 5,227,170 A | | 7/1993 | Sullivan |
| 5,230,899 A * | | 7/1993 | Park et al. ..................... 424/450 |
| 5,316,771 A | | 5/1994 | Barenholz et al. |
| 5,415,869 A | | 5/1995 | Straubinger et al. |
| 5,580,575 A | | 12/1996 | Unger et al. |
| 5,589,189 A * | | 12/1996 | Moynihan ..................... 424/450 |
| 5,653,998 A | | 8/1997 | Hamann et al. |
| 5,660,855 A * | | 8/1997 | Male-Brune .................. 424/450 |
| 5,676,928 A | | 10/1997 | Klaveness et al. |
| 5,684,169 A | | 11/1997 | Hamada et al. |
| 5,693,336 A * | | 12/1997 | Moynihan ..................... 424/450 |
| 5,747,060 A * | | 5/1998 | Sackler et al. ................ 424/426 |
| 5,795,896 A | | 8/1998 | Lofroth et al. |
| 5,830,865 A | | 11/1998 | Sternfelt et al. |
| 5,972,379 A * | | 10/1999 | Guo et al. ...................... 424/450 |
| 5,989,583 A * | | 11/1999 | Amselem ....................... 424/439 |
| 6,096,331 A | | 8/2000 | Desai et al. |
| 6,103,259 A * | | 8/2000 | Roux et al. .................... 424/450 |
| 6,146,659 A | | 11/2000 | Rahman |
| 6,447,800 B2 * | | 9/2002 | Hope ............................. 424/450 |
| 6,538,020 B2 | | 3/2003 | Joshi-Hangal et al. |
| 6,538,032 B1 * | | 3/2003 | Namgoong et al. .......... 514/642 |
| 6,599,527 B1 | | 7/2003 | Leigh et al. |
| 7,217,770 B2 | | 5/2007 | Seo et al. |
| 7,811,602 B2 | | 10/2010 | Cullis et al. |
| 7,850,990 B2 | | 12/2010 | Tardi et al. |
| 2002/0039556 A1 | | 4/2002 | Dyvik et al. |
| 2002/0051813 A1* | | 5/2002 | Boni et al. ..................... 424/450 |
| 2002/0094344 A1* | | 7/2002 | Hope ............................. 424/450 |
| 2002/0103254 A1 | | 8/2002 | Joshi-Hangal et al. |
| 2002/0120015 A1 | | 8/2002 | Dennis et al. |
| 2003/0049302 A1 | | 3/2003 | Pauletti et al. |
| 2003/0113369 A1 | | 6/2003 | Martin et al. |
| 2003/0129222 A1 | | 7/2003 | Lopez-Berstein et al. |
| 2003/0138481 A1 | | 7/2003 | Zadi |
| 2004/0071775 A1 | | 4/2004 | Jiang et al. |
| 2004/0126886 A1 | | 7/2004 | Kan et al. |
| 2005/0123594 A1 | | 6/2005 | Awasthi et al. |
| 2005/0142178 A1* | | 6/2005 | Daftary et al. ................ 424/450 |
| 2006/0014699 A1 | | 1/2006 | Edman et al. |
| 2006/0110441 A1 | | 5/2006 | Wong et al. |
| 2006/0172003 A1* | | 8/2006 | Meers et al. .................. 424/450 |

(Continued)

FOREIGN PATENT DOCUMENTS

DE    1920765 A1    5/1970
EP    0173494       3/1986

(Continued)

OTHER PUBLICATIONS

Madden, T.D., et al in BBA, 817, pp. 67-74, 1985.*
Takahashi, M. et al., Efficient preparation of liposomes encapsulating food materials using lecithins by a mechanochemical method, J Oleo Sci. 2007;56(1):35-42.
Takahashi, M. et al., Characterization and bioavailability of liposomes containing a ukon extract, Biosci Biotechnol Biochem. May 2008;72(5):1199-205.
Takahashi, M. et al., Liposomes encapsulating Aloe vera leaf gel extract significantly enhance proliferation and collagen synthesis in human skin cell lines, J Oleo Sci. 2009;58(12):643-50.
Thompson, A. K., et al., Preparation of liposomes from milk fat globule membrane phospholipids using a microfluidizer, J Dairy Sci. Feb. 2006;89(2):410-9.
Barnadas-Rodriquez, R., et al., Factors involved in the production of liposomes with a high-pressure homogenizer, Int J Pharm. Feb. 1, 2001;213(1-2):175-86.

(Continued)

*Primary Examiner* — Gollamudi Kishore
(74) *Attorney, Agent, or Firm* — Posternak Blankstein & Lund LLP

(57) ABSTRACT

Provided herein are methods for preparing liposomes and uses thereof. In certain embodiments, liposomes are prepared without using heat, organic solvents, proteins, and/or inorganic salts in the process. In certain embodiments, the liposomal preparation contains one or more active agents. In certain embodiments, the liposomal preparations are used in the treatment of diseases or disorders.

21 Claims, No Drawings

(56) References Cited

U.S. PATENT DOCUMENTS

| | | | |
|---|---|---|---|
| 2006/0222696 A1* | 10/2006 | Okada et al. | 424/450 |
| 2007/0292496 A1 | 12/2007 | Herrero Varnell et al. | |
| 2008/0102109 A1* | 5/2008 | Augustine et al. | 424/450 |
| 2008/0274172 A1* | 11/2008 | Moscoso Del Prado et al. | 424/450 |
| 2008/0286352 A1* | 11/2008 | Kumar et al. | 424/450 |
| 2009/0041833 A1* | 2/2009 | Bettinger et al. | 424/450 |
| 2009/0162425 A1 | 6/2009 | Divi et al. | |
| 2009/0191259 A1* | 7/2009 | Li et al. | 424/450 |
| 2009/0220587 A1 | 9/2009 | Allon et al. | |
| 2009/0221953 A1* | 9/2009 | Kajimoto et al. | 604/20 |
| 2009/0291129 A1 | 11/2009 | Parmar | |
| 2011/0177156 A1 | 7/2011 | Szoka et al. | |
| 2012/0107391 A1* | 5/2012 | Kelsey | 424/450 |

FOREIGN PATENT DOCUMENTS

| | | |
|---|---|---|
| EP | 0249561 B1 | 12/1987 |
| EP | 0670166 A2 | 9/1995 |
| EP | 0923943 A1 | 6/1999 |
| EP | 1151755 A1 | 11/2001 |
| EP | 1547582 A1 | 6/2005 |
| JP | 3101614 A | 4/1991 |
| WO | 9210166 | 6/1992 |
| WO | 95/12385 A1 | 5/1995 |
| WO | 97/20041 A1 | 6/1997 |
| WO | 97/30695 A1 | 8/1997 |
| WO | 99/04787 A1 | 2/1999 |
| WO | 99/13914 A1 | 3/1999 |
| WO | 99/45918 A1 | 9/1999 |
| WO | 99/49848 A1 | 10/1999 |
| WO | 00/00179 A1 | 1/2000 |
| WO | 00/03753 A2 | 1/2000 |
| WO | 00/40238 A1 | 7/2000 |
| WO | 00/71163 A1 | 11/2000 |
| WO | 01/01960 A1 | 1/2001 |
| WO | 01/05372 A2 | 1/2001 |
| WO | 01/30448 A1 | 5/2001 |
| WO | 01/87345 A1 | 11/2001 |
| WO | 02/07712 A2 | 1/2002 |
| WO | 02/43765 A2 | 6/2002 |
| WO | 02/080883 A2 | 10/2002 |
| WO | 03/033592 A1 | 4/2003 |
| WO | 03/045357 A1 | 6/2003 |
| WO | 2004/002468 A1 | 1/2004 |
| WO | 2004/047802 A2 | 6/2004 |
| WO | 2004/071466 A2 | 8/2004 |
| WO | 2005/000271 A1 | 1/2005 |

OTHER PUBLICATIONS

Jahn, A., et al., Unexpectedly High Entrapment Efficiencies in Nanometer Scale Liposomes With Hydrodynamic Focusing Using Continuous-Flow Microfluidics, Twelfth International Conference on Miniaturized Systems for Chemistry and Life Sciences, Oct. 12-16, 2008, San Diego, California, USA.
Yousefi, A., et al., Preparation and In Vitro Evaluation of a Pegylated Nano-Liposomal Formulation Containing Docetaxel, Sci Pharm. 2009;77:453-464.
Baedelmeijer, H. A., et al., Entrapment by Cremophor EL decreases the absorption of paclitaxel from the gut, Cancer Chemother Pharmacol. Feb. 2002:49(2):119-25.
O'Reilly, J. R., et al., The effect of mixed micellar systems, bile salt/fatty acids, on the solubility and intestinal absorption of clofazimine (B663) in the anaesthetised rat, International Journal of Pharmaceutics, 1994;109:147-154.
Pinnamaneni, S., et al., Formulation approaches for orally administered poorly soluble drugs, Pharmazie. May 2002;57(5):291-300.
Gustafsson, D., et al., The Direct Thrombin Inhibitor Melagatran and Its Oral Prodrug H 376/95: Intestinal Absorption Properties, Biochemical and Pharmacodynamic Effects, Thromb Res. Feb. 1, 2001;101(3):171-81.
European Journal of Hospital Pharmacists, Advances in Anticoagulant Care for the Prevention of Venous Thromboembolic Events After Othopaedic Surgery: A Pharmaceutical Persepctive on Ximelagatran, a Novel Oral Direct Thrombin Inhibitor, 2004;Scientific Section(5):264-270.
Szelag, H., et al., The behaviour of modified monoacylglycerol emulsifiers in emulsion systems, Colloids and Surfaces A: Physicochemical and Engineering Aspects, 1999;155:349-357.
Solomons, Organic Chemistry, 5th Edition, John Wiley & Sons, Inc., New York, 1992:1049-1052.
Nasongkla, N., et al., Enhancement of solubility and bioavailability of beta-lapachone using cyclodextrin inclusion complexes, Pharm Res. Oct. 2003;20(10):1626-33.
Non-final office action for related U.S. Appl. No. 10/834,816 dated Oct. 26, 2006.
Final office action for related U.S. Appl. No. 10/834,816 dated Mar. 30, 2007.
Non-final office action for related U.S. Appl. No. 10/834,816 dated Sep. 10, 2007.
Notice of Allowance for related U.S. Appl. No. 10/834,816 dated Jan. 7, 2008.
Non-final office action for related U.S. Appl. No. 11/591,6606 dated Jul. 5, 2007.
Non-final office action for related U.S. Appl. No. 11/591,6606 dated Jan. 9, 2008.
Notice of Allowance for related U.S. Appl. No. 11/591,6606 dated Jun. 3, 2008.
Notice of Allowance dated Jul. 24, 2013 received in copending U.S. Appl. No. 12/889,305.
Non-Final Office Action dated Nov. 19, 2012 received in copending U.S. Appl. No. 12/889,265.
Non-Final Office Action dated Nov. 15, 2012 received in co-pending U.S. Appl. No. 12/889,305.
Trosko, et al., Mechanism of up-regulated gap junctional intercellular communication during chemoprevention and chemotherapy of cancer, Mutation Research, 2001; 480-481:219-229.
Ahmad, M. U., et al., Guggullipid derivatives: synthesis and applications, Chemistry and Physics of Lipids 163 (2010) 362-366.
Final Office Action dated Apr. 4, 2013 received in copending U.S. Appl. No. 12/889,305.
Takada et al., "Enhanced selective lymphatic delivery of cyclosporin a by solubilizers and intensified immunosuppressive activity against mice skin allograft," (1986) 3(1):48-51.
Dordunoo et al., International Journal of Pharmaceutics, Solubility and Stability of Taxol: Effects of Buffers and Cyclodextrins (1996) 133:191-201.
Non-Final Office Action dated Nov. 19, 2012 received in co-pending U.S. Appl. No. 12/889,265.

\* cited by examiner

METHODS FOR THE PREPARATION OF LIPOSOMES

CROSS REFERENCE TO RELATED APPLICATIONS

This application claims the benefit under 35 U.S.C. §119 of U.S. Provisional Patent Appl. No. 61/245,185, filed Sep. 23, 2009, the disclosure of which is incorporated by reference in its entirety herein.

BACKGROUND

The bioavailability of a pharmaceutical drug depends largely in part on the solubility and stability of the drug. Many methods have been employed to improve bioavailability of a drug, including, but not limited to, pH adjustment, associating the drug in micelles of detergents, solubilization in an organic solvent, complexation with cyclodextrin or other polymers, and encapsulating the drug in a liposome bilayer (Strickley, R. G., *Pharmaceutical Research*, No. 21, 2004: 201-230). Either the drug itself or the excipients used to solubilize the drug may have side effects such as allergic reaction or hemolysis.

It is known that the solvents (e.g., ethanol, propylene glycol, polyethylene glycol, dimethylacetamide, dimethylsulfoxide ("DMSO")), complexing agents (for example, nicotinamide), and surfactants (for example, sodium oleate) are hemolytic and are therefore undesirable for use in injectable solutions. Other limitations to using organic solvents in injectable products include precipitation, pain, and inflammation upon injection.

Liposomes are microscopic lipid vesicles that are composed of a central aqueous cavity surrounded by a lipid membrane formed by concentric bilayer(s) (lamellas). Liposomes are able to incorporate hydrophilic substances (in the aqueous interior) or hydrophobic substances (in the lipid membrane). Liposomes can be unilamellar vesicles ("UMV"), having a single lipid bilayer, or multilamellar vesicles ("MLV"), having a series of lipid bilayers (also referred to as "oligolamellar vesicles"). The multilamellar vesicles typically range in size from 0.2 μm to 10 μm in diameter. See e.g., WO 98/006882. Although anti-hemolytic measures are commonly taken in formulations, maintaining a sufficient amount of liposome in formulation may not be feasible due to the incompatibility of the liposome with an excipient, or the instability of the liposome in the formulation. Further, reconstituting lyophilized formulations containing hydrophobic drugs is often difficult. Moreover, liposomes are not stable in formulations containing concentrated organic solvents.

Unilamellar vesicles with a diameter of less than 0.2 μm (e.g. between 0.02 and 0.2 μm) are commonly known as small unilamellar vesicles ("SUV"). Unilamellar vesicles with a diameter greater than 0.45 μm (in some cases greater than 1 μm) are commonly known as large unilamellar vesicles ("LUV").

The bilayer(s) of liposomes most often comprise phospholipids, but may also comprise lipids including but not limited to fatty acids, fatty acid salts and/or fatty alcohols. The properties of the liposomes depend, among other factors, on the nature of the constituents. Consequently, if liposomes with certain characteristics are to be obtained, the charge of its polar group and/or the length and the degree of saturation of its fatty acid chains must be taken into account.

In addition, the properties of liposomes may be modified, e.g., to incorporate cholesterol and other lipids into the membrane, change the number of lipidic bilayers, or covalently join natural molecules (e.g., proteins, polysaccharides, glycolipids, antibodies, enzymes) or synthetic molecules (e.g., polyethyl glycol) to the surface. There are numerous combinations of phospholipids, optionally with other lipids or cholesterol, in an aqueous medium to obtain liposomes. Depending on the method of preparation and the lipids used, it is possible to obtain vesicles of different sizes, structures, and properties.

Another important parameter to consider with respect to the formation of liposomes is the rigidity of the lipidic bilayer. The hydrated lipid that focus part of the bilayer may be in either a liquid-crystalline (fluid) or gel state. As the temperature increases, the gel state is converted into the liquid-crystalline state. This occurs at a temperature known as the transition temperature (Tc), which is specific to each lipid. The Tc is directly proportional to chain length and inversely proportional to the degree of unsaturation of the fatty acids and depends on the nature of the polar group.

Despite this, common methods in the preparation of lipid vesicles, such as liposomes, comprise evaporating an organic solvent in which the lipids are dissolved and then dispersed in an optionally buffered aqueous solution. One exemplary method, known as the Bangham method, was originally described in Bangham et al., *J. Mol. Biol.*, 11:238-252 (1965). Variations of the Bangham method are known by those skilled in the art, some of which are described below.

Hydration of a thin lipidic layer. Starting with the organic solution of the constituent lipids of the bilayer, a lipidic film is prepared through removal of organic solvent, which can be achieved by means of evaporation (e.g., at reduced pressure in a rotary evaporator) or by lyophilization. The dry lipidic film obtained is hydrated by adding an aqueous solution and agitating the mixture at temperatures above the Tc.

Reverse-phase evaporation. Starting with the organic solution of the constituent lipids of the bilayer, a lipidic film is prepared through removal of the organic solvent. The system is purged with nitrogen and the lipids are re-dissolved in a second organic solution, usually constituted by diethyl ether and/or isopropyl ether. The aqueous phase is added to the re-dissolved lipids. The system is maintained under continuous nitrogen. A gel is formed by removing the second organic solvent.

Solvent injection. The lipids, dissolved in an organic solvent, are injected slowly into an aqueous solution. The organic solvent used is often a water-miscible solvent, and the aqueous solution may be warmed.

Additional methods for the preparation of multilamellar vesicles can be found, e.g., in Szoka and Papandjopoulos, *Ann. Rev. Biophys. Bioeng.*, 2: 467-508 (1980), and Dousset and Douste-Blazy, Les Liposomes, Puisieux and Delattre, Editors, Tecniques et Documentation Lavoisier, Paris, pp. 1-73 (1985).

Further, when the incorporation of more than one lipid is desired, the lipids should remain homogeneously distributed in the liposomal vesicles. Traditionally, this is achieved by previously dissolving the lipids in an organic solvent and using the resulting organic solvent for preparing the liposomes.

U.S. Pat. No. 4,508,703 describes a method for obtaining powdery mixtures of at least one amphyphilic lipid and, optionally, at least one component of a hydrophobic or partially hydrophobic nature, a method which includes dissolving the components of the mixture in at least one organic solvent and atomizing the obtained solution into an inert gas. The method permits the preparation of lipidic mixtures which can be easily dispersed in an aqueous medium but does not avoid the use of organic solvents.

WO 92/10166 describes a method for preparing liposomes with an elevated encapsulation capacity. The method permits the use of mixtures of lipids; however, the mixture is obtained by means of previous dissolution of the lipids in an organic solvent and subsequent evaporation. In addition, the contact between the lipids and the aqueous solution of active agent is carried out at a temperature above the Tc.

Moreover, it is reported that, where liposomes are made without using organic solvents, other manipulations, which may result in formulations with certain unfavorable characteristics, are generally required. For example, U.S. Pat. App. Pub. No. 2008/0274172 describes methods of preparing liposomes containing at least two phospholipids without using organic solvents. However temperatures above the Tc were used to obtain stable liposomes from aqueous solutions containing inorganic salts.

Consequently, existing methods for preparing liposomes utilize organic solvents, protein, inorganic salts, and/or heat. Due to their toxicity and flammability, organic solvents are undesirable in the preparation of liposomes for pharmaceutical, cosmetic and other uses. Moreover, the use of organic solvents and proteins has negative repercussions in terms of production costs, safety, work hygiene and the environment. Similarly, the use of heat in the preparation of liposomes is undesirable in terms of production costs, safety, and the environment. The use of inorganic salts in the preparation of liposomes is undesirable as the introduction of inorganic salts increases the size of the liposome and/or results in a more turbid formulation. See e.g. Castile et al., *International Journal of Pharmaceutics*, 1999, vol. 188, issue 1, pp. 87-95. Thus, there is a need for a method for preparing liposomes without the use of undesirable agents and procedures.

SUMMARY

Provided herein are methods for preparing liposomes. In certain embodiments, liposomes are prepared without using heat, organic solvents, proteins, and/or inorganic salts in the process.

In one embodiment, a method is provided for the preparation of liposomes, the method comprising:
(a) Combining one or more lipids in an aqueous medium at ambient temperature;
(b) Dispersing the lipids in the aqueous medium; and
(c) Adding one or more sugars to the resulting mixture, thereby forming a solution of liposomes.

In certain embodiments, the liposomal preparation contains one or more active agents. In certain embodiments, the active agent is a pharmaceutical agent. In certain embodiments, active agents include, but are not limited to lapachone; transferrin; cyclosporine; colchicine; and combinations of lapachone and transferrin in a single liposome formulation.

In certain embodiments, the one or more active agents are added after the liposome or solution of liposomes has been prepared. In other embodiments, the one or more active agents are added during formation of the liposome.

Also provided herein are uses of liposomal preparations in the treatment of diseases or disorders. In one embodiment, the liposomal preparation is suitable for parenteral administration to a patient suffering from said disease or disorder. In one embodiment, the patient is a human.

DEFINITIONS

As used herein, and unless otherwise specified, "lipid" is understood to be a fatty acid, fatty acid salt, fatty alcohol, or phospholipid. Lipids may also be read to include sterols, including, but not limited to, cholesterol; sphingolipids, including, but not limited to, sphingomyelin; glycosphingolipids including, but not limited to, gangliosides, globocides and cerebrosides; and surfactant amines including, but not limited to, stearyl, oleyl and linoleyl amines.

As used herein, and unless otherwise specified, "phospholipid" is understood to be an amphyphilic derivative of glycerol, in which one of its hydroxyl groups is esterified with phosphoric acid and the other two hydroxyl groups are esterified with long-chain fatty acids that can be equal to or different from each other and can be saturated or unsaturated. A neutral phospholipid is generally one in which the other phosphoric acid hydroxyl is esterified by an alcohol substituted by a polar group (usually hydroxyl or amino) and whose net charge is zero. A phospholipid with a charge is generally one in which the other phosphoric acid hydroxyl is esterified by an alcohol substituted by a polar group and whose net charge is positive or negative.

Examples of phospholipids include, but are not limited to phosphatidic acid ("PA"), phosphatidylcholine ("PC"), phosphatidylglycerol ("PG"), phophatidylethanolamine phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimnyristoylphosphatidylinositol ("DMPI") dioleoylphosphatidylinositol ("DOPI"), dipalmitoylphosphatidylinositol ("DPPI"), distearoylphosphatidylinositol ("DSPI"), 1-palmitoyl-2-olcoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSP"), 1-palmitoyl-2-olcoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

As used herein, and unless otherwise specified, "encapsulate" or "encapsulation" is understood to be the process of incorporating an active agent into liposomes or liposomal vesicles. The encapsulated active agent can remain in the aqueous interior or associate with membranes.

As used herein, and unless otherwise specified, the term "enhance" or "enhancing," when used in connection with the solubility of a compound, means that the methods provided herein result in the increased solubility of the compound as compared to the solubility of the same compound in water. Specifically, the term "enhance" or "enhancing" means that, when the methods provided herein are used, the solubility of a compound increases about 20 percent or more, about 40 percent or more, about 60 percent or more, about 80 percent or more, about 100 percent or more, or about 200 percent or more of the solubility of the same compound in a reference solvent. In some embodiments, the reference solvent is water.

As used herein, and unless otherwise specified, the term "hydrophobic compound" means a compound with little or no water solubility. In some embodiments, a hydrophobic compound has an intrinsic water solubility (i.e., water solubility of the unionized form) of less than about 20 percent by weight, about 15 percent by weight, about 10 percent by weight, about 5 percent by weight, about 1 percent by weight, about 0.1 percent by weight or about 0.01 percent by weight. In other embodiments, a hydrophobic compound has an intrinsic water solubility of less than about 10 mg/mL, about 7 mg/mL, about 5 mg/mL, about 3 mg/mL, about 1 mg/mL or about 0.1 mg/mL.

As used herein, or unless otherwise specified, the terms "aqueous medium" or "aqueous media" include any water based medium, e.g., water, saline solution, a sugar solution, a transfusion solution, a buffer, and any other readily available water-based medium. Further, an aqueous medium may contain one or more water soluble organic solvents. In the case of a parenteral solution, an aqueous medium is preferably sterile and suitable for use as a carrier of an active agent. Examples of aqueous media include, but are not limited to, water for injection, saline solution, Ringer's solution, D5W, or other solutions of water-miscible substances such as dextrose and other electrolytes.

As used herein, and unless otherwise specified, the term "fatty acid" means a compound whose structure is a carboxylic group attached to a hydrocarbon chain having one or more carbon atoms. The hydrocarbon chain may be saturated or unsaturated (i.e., alkyl, alkenyl or alkynyl hydrocarbon chains). Also, the hydrocarbon chain may be straight or branched. Moreover, in some embodiments, hydrogens in the hydrocarbon chain may be substituted.

As used herein, and unless otherwise specified, the term "fatty alcohol" means a compound whose structure is an alcohol group attached to a hydrocarbon chain having one or more carbon atoms. The hydrocarbon chain may be saturated or unsaturated (i.e., alkyl, alkenyl or alkynyl hydrocarbon chains). Also, the hydrocarbon chain may be straight or branched. Moreover, in some embodiments, hydrogens in the hydrocarbon chain may be substituted.

As used herein, and unless otherwise specified, the term "fatty acid salt" means a compound formed from a reaction between a fatty acid and an inorganic/organic base. In addition, the term encompasses a compound formed from a reaction between a fatty alcohol and an inorganic/organic acid. Examples of such acids include, but are not limited to, sulfuric and phosphoric acid. The hydrocarbon chain of the fatty acid salt may be saturated or unsaturated (i.e., alkyl, alkenyl or alkynyl hydrocarbon chains). In addition, the hydrocarbon chain may be straight or branched. Moreover, in some embodiments, hydrogens in the hydrocarbon chain may be substituted.

As used herein, and unless otherwise specified, the term "substituted" means a group substituted by one or more substituents including, but not limited to, alkyl, alkenyl, alkynyl, cycloalkyl, aroyl, halo, haloalkyl (e.g., trifluoromethyl), substituted or unsubstituted heterocycloalkyl, haloalkoxy (e.g., trifluoromethoxy), hydroxy, alkoxy, cycloalkyloxy, heterocylooxy, oxo, alkanoyl, aryl, substituted aryl, substituted or unsubstituted heteroaryl (e.g., indolyl, imidazolyl, furyl, thienyl, thiazolyl, pyrrolidyl, pyridyl, pyrimidyl and the like), arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino, alkanoylamino, aroylamino, aralkanoylamino, substituted alkanoylamino, substituted arylamino, substituted aralkanoylamino, carbamyl (e.g., $CONH_2$), substituted carbamyl (e.g., CONH-alkyl, CONH-aryl, CONH-arylalkyl or instances where there are two substituents on the nitrogen), carbonyl, alkoxycarbonyl, carboxy, cyano, ester, ether, guanidino, nitro, sulfonyl, alkylsulfonyl, arylsulfonyl, arylalkylsulfonyl, sulfonamido (e.g. $SO_2NH_2$), substituted sulfonamido, thiol, alkylthio, arylthio, arylalkylthio, cycloalkylthio, heterocyclothio, alkylthiono, arylthiono and arylalkylthiono.

As used herein, and unless otherwise specified, the term "alkyl" means a saturated straight chain or branched non-cyclic hydrocarbon having 1-20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, and unless otherwise specified, the term "alkenyl" means a straight chain or branched non-cyclic hydrocarbon having 2-20 carbon atoms, preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, and unless otherwise specified, the term "alkynyl" means a straight chain or branched non-cyclic hydrocarbon having 2-20 carbon atoms, preferably 2-10 carbon atoms, most preferably 2-6 carbon atoms, and including at lease one carbon-carbon triple bond. Representative straight chain and branched ($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, and unless otherwise specified, the term "pharmaceutically acceptable salt" refers to a salt prepared from pharmaceutically acceptable non-toxic acids or bases including inorganic acids and bases and organic acids and bases. Suitable pharmaceutically acceptable base addition salts for the compositions provided herein include, but are not limited to, metallic salts made from aluminum, calcium, lithium, magnesium, potassium, sodium, and zinc, or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see e.g., *Remington's Pharmaceutical Sciences*, 18$^{th}$ ed., Mack Publishing, Easton Pa. (1990) or Remington: The Science and Practice of Pharmacy, 19th ed., Mack Publishing, Easton Pa. (1995).

As used herein, the term "hydrate" means a compound provided herein, or a salt thereof, that further includes a stoichiometric or non-stoichiometric amount of water bound by non-covalent intermolecular forces.

As used herein, the term "clathrate" means a compound provided herein, or a salt thereof in the form of a crystal lattice that contains spaces (e.g., channels) that have a guest molecule (e.g., a solvent or water) trapped within.

As used herein, and unless otherwise indicated, the term "prodrug" means a derivative of a compound that can hydrolyze, oxidize, or otherwise react under biological conditions (in vitro or in vivo) to provide an active compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. Esterifying any of the carboxylic acid moieties present on the molecule conveniently forms the carboxylate esters. Prodrugs can typically be prepared using well-known methods, such as those described by Burger's Medicinal Chemistry and Drug Discovery 6th ed. (Donald J. Abraham ed., 2001, Wiley), and Design and Application of Prodrugs (H. Bundgaard ed., 1985, Harwood Academic Publishers Gmfh).

As used herein, and unless otherwise specified, the term "stable," when used in connection with a formulation, means that the active agent of the formulation, when prepared using the methods provided herein, remains solubilized for a specified amount of time and does not significantly degrade or aggregate or become otherwise modified (e.g., as determined by HPLC).

As used herein, and unless otherwise specified, "temperature below the Tc" is understood to be a temperature which is lower than the Tc of the lipid having the lowest Tc, and "temperature greater than the Tc" is understood to be a temperature which is greater than the Tc of the lipid having the highest Tc.

As used herein, and unless otherwise specified, the term "harmful ingredient," when used in connection with pharmaceutical compositions, means an ingredient commonly used in a pharmaceutical composition that may cause clinical side effects such as, but not limited to, hemolysis, hypersensitive reaction, peripheral neuropathies, and/or decrease in the bioavailability of the active ingredient of the composition. Examples of harmful ingredients include, but are not limited to: toxic solvents, including organic solvents such as ethanol, methanol, 1-propanol, 2-propanol, acetone, acetonitrile, ethyl acetate, methyl acetate, diethyl ether, dimethyl ether, diisopropyl ether, methyl tert-butyl ether ("MTBE"), tetrahydrofuran ("THF"), dichloromethane, chloroform, carbon tetrachloride, 1,2-dicholroethane, pentane, hexanes, heptane, petroleum ether, dioxane, ethylene glycol, diethylene glycol, diglyme, 1,2-dimethoxyethane, 1-butanol, 2-butanol, 2-butanone, benzene, toluene, dimethylsulfoxide ("DMSO"), dimethylformamide ("DMF"), hexamethylphosphoramide ("HMPA"), N-methylpyrrolidone, glycerin, nitromethane, triethyl amine, xylenes, CREMOPHOR® EL, and polyethylene glycol ("PEG"); co-detergents or surfactants such as polysorbates (e.g., Tweens) or vitamin E; oils such as Castor oil or corn oil; proteins such as HSA; or any other biologic which is potential source of contamination.

DETAILED DESCRIPTION

Provided herein is a method for the preparation of liposomes, the method comprising:

(a) Combining one or more lipids in an aqueous medium at ambient temperature;

(b) Dispersing the lipids in the aqueous medium; and (c) Adding one or more sugars to the resulting mixture, thereby forming a solution of liposomes.

In another embodiment, at step (b), the method further comprises homogenization of the lipids in the aqueous medium.

Some embodiments further comprise a step (d), wherein one or more active agents is added to the solution of liposomes. In one embodiment, the active agent is a hydrophobic drug. In one embodiment, the active agent is added as a solid. In another embodiment, the active agent is added in an organic solvent. In another embodiment, the active agent is added in organic solvent which further comprises one or more fatty acid salts, fatty acids and/or phospholipids.

In another embodiment, the active agent is added during formation of the liposome.

In certain embodiments, the resulting liposomes are less than about 1 µm in diameter.

In one embodiment, the resulting liposomes are less than about 500 nm in diameter.

In one embodiment, the resulting liposomes are less than about 100 nm in diameter.

In one embodiment, at least one of the lipids is a phospholipid or a mixture of phospholipids. Examples of phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), di decanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinolcoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

The phospholipids provided herein may be chiral or achiral. The chiral phospholipids provided herein may be D- or L-phospholipids, for example, L-α-phosphatidylcholine or L-3-phosphatidylcholine.

In one embodiment, L-α-phosphatidylcholine is used in the methods provided herein.

In another embodiment, provided herein is a method for the preparation of liposomes, the method comprising:

(a) combining sodium oleate and L-α-phosphatidylcholine in an aqueous medium at ambient temperature;

(b) dispersing sodium oleate and L-α-phosphatidylcholine in the aqueous medium; and (c) adding one or more sugars to the resulting mixture, thereby forming a solution of liposomes.

In one embodiment, the aqueous medium contains one or more active agents, or pharmaceutically acceptable salts, hydrates, clathrates or prodrugs thereof. Examples of active agents include, but are not limited to, lapachone (β-lapachone), taxanes (including, but not limited to, taxol, 7-epi-taxol, 7-acetyl taxol, 10-desacetyltaxol, 10-desacetyl-7-epi-taxol, 7-xylosyltaxol, 10-desacetyl-7-sylosyltaxol, 7-glutaryltaxol, 7-N,N-dimethylglycycltaxol, 7-L-alanyl-taxol, taxotere, and mixtures thereof), paclitaxel, colchicine, transferrin, cyclosporines, cyclosporin A, ketoprofen, propofol, acetylsalicylic acid, acetaminophen, amphotericin, digoxin, doxorubicin, daunorubicin, epirubicin, idarubicin, angiogenesis inhibitors (e.g, bevacizumab, ranibizumab, vitaxin, carboxyamidotriazole, combretastatin A-4, fumagillin analogs (e.g., TNP-470), CM101, IFN-α, interleukin-10, interleukin-12, platelet factor-4, suramin, SU5416, thrombospondin, VEGFR antagonists, angiostatin, endostatin, 2-methoxyestradiol, tecogalan, thalidomide, prolactin, linomide, angiopoietin-1, basic fibroblast growth factor, vascular endothelial growth factor), vinca-alkaloids (e.g., vinblastine, vincristine, vindesin, etoposide, etoposide phosphate, and teniposide), cytarabine, actinomycin, etoposide, bleomycin, gentamycin, cyclophosphamide, methotrexate, streptozotocin, cytosine, β-D-arabinofuranoside-5'-triphosphate, cytochrome C, cisplatin, N-phosphono-acetyl-L-aspartic acid, 5-fluoroorotic acid, acyclovir, zidovudine, interferons, aminoglycosides, cephalosporins, tetracyclines, propranolol, timolol, labetolol, clonidine, hydralazine, imipramine, amitriptyline, doxepim, phenyloin, diphenhydramine, chlorphenirimine, promethazine, prostaglandins, methotrexate, progesterone, testosterone, estradiol, estrogen, epirubicin, beclomethasone and esters, vitamin E, cortisone, dexamethasone and esters, betamethasone valerete, biphenyl dimethyl dicarboxylic acid, calcitonins, camptothecin, captopril, cephazoline, chloroquinine, chlorothiazole, co-agulation factors VIII and IX, d-alpha-tocopherol, dexamethasone, dichlofenac, etoposide, feldene, flubiprofen, 5-fluorouracil, fluoxetine, fusidic acid, gentamicin, glyburide, granisetron, growth hormones, indomethacin, insulin, itraconazole, ketoconazole, methotrexate, metronidazole, minoxidil, mitomycin, nafcillin, naproxen, ondansetron, oxyphenbutazone, parazosin, physostigmine, piroxicam, prednisolone, primaquine, quinine, ramipril, taxotane, tenoxicam, terazosin, triamcinolone, urokinase, opioid analgesics (e.g., alfentanil, anileridine, codiene, diamorphine, fentanyl, hydrocodone, hydromorphone, meperidine, morphine, oxycodone, oxymorphone, propoxyphene, sufentanil, pentazocine and nalbuphine), non-steroidal anti-inflammatory drugs (e.g., aspirin, indometacin, ibuprofen, mefenamic acid and phenylbutazone), angiotensin converting enzyme ("ACE") inhibitors (e.g., captoprilpolyene), protein kinase C inhibitors, antibiotics (e.g., imidazole and triazole antibiotics), folic acid, anthracycline antibiotics, anti-sense RNAs, tricathecums, microbial ribosomal-inactivating toxins (e.g., gelonin, abrin, ricin A chain, *Pseudomonas* exotoxin, diptheria toxin, pokeweed antiviral peptide), pipecolic acid derivatives (e.g., tacrolimus), plant alkaloids, dyes, radioisotope-labeled compounds, radiopaque compounds, radiosensitizers (e.g., 5-chloro-2'-deoxyuridine, 5-bromo-2'-deoxyuridine and 5-iodo-2'-deoxyuridine), fluorescent compounds, mydriatic compounds, bronchodilators, local anesthetics (e.g., dibucaine and chlorpromazine), antifungal agents (e.g., miconazole, terconazole, econazole, isoconazole, butaconazole, clotrimazole, itraconazole, nystatin, naftifine and amphotericin B), antiparasitic agents, hormones, hormone antagonists, immunomodulators, neurotransmitter antagonists, anti-diabetic agents, antiglaucoma agents, vitamins, narcotics, and imaging agents. For additional disclosure of active agents, see Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996.

In one embodiment, the active agent is a hydrophobic compound, or a compound with poor solubility in water.

In another embodiment, the active agent is a non-hydrophobic compound.

In one embodiment, the active agent is a water soluble membrane-impermeant agent such as a peptide, a protein, a nucleic acid, a nucleotide, a nucleoside, a carbohydrate or an analog thereof.

In one embodiment, the aqueous medium does not contain an active agent.

In another embodiment, the resulting solution contains 10% by weight trehalose.

In another embodiment, the active agent is lapachone, or a pharmaceutically acceptable salt, hydrate, clathrate or prodrug thereof.

In another embodiment, the active agent is transferrin, or a pharmaceutically acceptable salt, hydrate, clathrate or prodrug thereof.

In another embodiment, the active agent is cyclosporine, or a pharmaceutically acceptable salt, hydrate, clathrate or prodrug thereof.

In one embodiment, the active agents are transferrin and lapachone, or pharmaceutically acceptable salts, hydrates, clathrates or prodrugs thereof.

Examples of sugars that may be used in the methods provided herein include, but are not limited to, sucrose, glucose, fructose, lactose, maltose, mannose, galactose and trehalose.

In one embodiment, the sugar is trehalose.

In one embodiment, the liposomal preparation is suitable for parenteral administration to a patient suffering from one or more diseases or disorders.

In one embodiment, the patient is a human.

In certain embodiments, the sequence of the addition of active agent(s) results in enhanced solubility of the active agent(s). The conventional method of incorporating hydrophobic drug to liposome is by adding the drug to lipid before liposome preparation. See, e.g., Immordino, M. L. et al., *Journal of Controlled Release*, 2003, 91: 417-429. By the conventional process, the incorporation of the drug is only 0.3 to 0.7 mg/mL.

Provided herein are methods for the preparation of liposomes wherein the addition of the active agent(s) after fogillation of the liposome results in enhanced solubility of the active agent(s). In one embodiment, the solubility of the active agent(s) in liposome is increased by at least about two-fold, five-fold or ten-fold compared to the conventional process. In one embodiment, the solubility of the active agent(s) in liposome is increased to about 5 mg/mL.

In certain embodiments in which the active agent is a hydrophobic drug, the active agent is added to pre-made liposome as a solid or in an organic solvent. In one embodiment, the pre-made liposome comprises one or more fatty acid salts, fatty acids and/or phospholipids to increase the solubility of the active agent.

In one embodiment, the sequence of the addition of active agent(s) results in greater efficiency of incorporation of the active agent(s) into liposome. In certain embodiments, the efficiency of incorporation into liposome is 50%, 60%, 70%, 80%, 90%, 95%, 98%, 99% or 100%. In certain embodiments, the efficiency of incorporation is 90%, 95%, 98%, 99% or 100%.

Without being limited to a particular theory or mechanism, the increase in incorporation of active agent to pre-made liposome (e.g., to a concentration of about 5 mg/mL) may be due to increase in surface area of liposome.

Also provided herein is a liposomal composition prepared by a method comprising:

(a) Combining one or more lipids in an aqueous medium at ambient temperature;

(b) Dispersing the lipids in the aqueous medium; and (c) Adding one or more sugars to the resulting mixture, thereby forming a solution of liposomes.

In another embodiment, provided herein is a liposomal composition prepared by a method comprising:

(a) Combining one or more lipids in an aqueous medium at ambient temperature;

(b) Dispersing the lipids in the aqueous medium;

(c) Adding one or more sugars to the resulting mixture, thereby forming a solution of liposomes; and (d) Adding an active agent to the solution of liposomes.

In one embodiment, the active agent is a hydrophobic drug.

In one embodiment, the active agent is added as a solid.

In one embodiment, the active agent is added in an organic solvent.

In one embodiment, the active agent in organic solvent further comprises one or more fatty acid salts, fatty acids and phospholipids.

In certain embodiments, the methods provided herein result in stable solutions, compositions or formulations comprising liposomes and one or more active agents. In these embodiments, the active agent(s) remain solubilized for a specified amount of time and do not significantly degrade, aggregate or become otherwise modified (e.g., as determined by HPLC).

In some embodiments, about 70 percent or greater, about 80 percent or greater or about 90 percent or greater of the active agent remains solubilized after a week after dilution with an acceptable diluent at an elevated temperature (e.g., about 35° C. or higher).

In other embodiments, about 70 percent or greater, about 80 percent or greater or about 90 percent or greater of the active agent remains solubilized after a week after dilution with an acceptable diluent at room temperature.

In other embodiments, about 70 percent or greater, about 80 percent or greater or about 90 percent or greater of the active agent remains solubilized after a week at a reduced temperature (e.g., about 10° C. or lower).

In certain embodiments, the methods provided herein result in enhanced solubility of an active agent, as compared to the solubility of the same active agent in an aqueous medium. Specifically, when the methods provided herein are used, the solubility of the active agent increases about 20 percent or more, about 40 percent or more, about 60 percent or more, about 80 percent or more, about 100 percent or more, or about 200 percent or more of the solubility of the same active agent in a reference solvent. In some embodiments, the reference solvent is water.

Also provided herein is a method of treating a disease or disorder using a liposomal composition provided herein. In some embodiments, the disease or disorder includes, but is not limited to, oncological disorders, proliferative disorders, central nervous system disorders, autoimmune disorders, and inflammatory diseases or disorders. In other embodiments the methods are directed to the treatment of bacterial, viral or fungal infections.

Proliferative disorders (e.g. cancer) that may be treated by the methods provided herein include, but are not limited to, neoplasms, tumors (malignant and benign) and metastases, or any disease or disorder characterized by uncontrolled cell growth. The cancer may be a primary or metastatic cancer. Specific examples of cancers that can be prevented, managed, treated or ameliorated in accordance with the methods of the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias (e.g., acute leukemia, acute lymphocytic leukemia), acute myelocytic leukemias (e.g., myeloblastic, promyelocytic, myelomonocytic, monocytic, erythroleukemia leukemias and myelodysplastic syndrome), chronic leukemias (e.g., chronic myelocytic (granulocytic) leukemia, chronic lymphocytic leukemia, hairy cell leukemia), polycythemia vera, lymphomas (e.g., Hodgkin's disease, non-Hodgkin's disease), multiple myelomas (e.g., smoldering multiple myeloma, nonsecretory myeloma, osteosclerotic myeloma, plasma cell leukemia, solitary plasmacytoma and extramedullary plasmacytoma), Waldenstrom's macroglobulinemia, monoclonal gammopathy of undetermined significance, benign monoclonal gammopathy, heavy chain disease, bone and connective tissue sarcomas (e.g., bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma), brain tumors (e.g., glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma), breast cancer (e.g., adenocarcinoma, lobular (small cell) carcinoma, intraductal carcinoma, medullary breast cancer, mucinous breast cancer, tubular breast cancer, papillary breast cancer, Paget's disease, and inflammatory breast cancer), adrenal cancer (e.g., pheochromocytom and adrenocortical carcinoma), thyroid cancer (e.g., papillary or follicular thyroid cancer, medullary thyroid cancer and anaplastic thyroid cancer), pancreatic cancer (e.g., insulinoma, gastrinoma, glucagonoma, vipoma, somatostatin-secreting tumor, and carcinoid or islet cell tumor), pituitary cancers (e.g., Cushing's disease, prolactin-secreting tumor, acromegaly, and diabetes insipius), eye cancers (e.g., ocular melanoma such as iris melanoma, choroidal melanoma, and ciliary body melanoma, and retinoblastoma), vaginal cancers (e.g., squamous cell carcinoma, adenocarcinoma, and melanoma), vulvar cancer (e.g., squamous cell carcinoma, melanoma, adenocarcinoma, basal cell carcinoma, sarcoma, and Paget's disease), cervical cancers (e.g., squamous cell carcinoma, and adenocarcinoma), uterine cancers (e.g., endometrial carcinoma and uterine sarcoma), ovarian cancers (e.g., ovarian epithelial carcinoma, borderline tumor, germ cell tumor, and stromal tumor), esophageal cancers (e.g., squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma), stomach cancers (e.g., adenocarcinoma, fungaling (polypoid), ulcerating, superficial spreading, diffusely spreading, malignant lymphoma, liposarcoma, fibrosarcoma, and carcinosarcoma), colon cancers, rectal cancers, liver cancers (e.g., hepatocellular carcinoma and hepatoblastoma, gallbladder cancers such as adenocarcinoma), cholangiocarcinomas (e.g., pappillary, nodular, and diffuse), lung cancers (e.g., non-small cell lung cancer, squamous cell carcinoma (epidermoid carcinoma), adenocarcinoma, large-cell carcinoma and small-cell lung cancer), testicular cancers (e.g., germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma), penile cancers, oral cancers (e.g., squamous cell carcinoma), basal cancers, salivary gland cancers (e.g., adenocarcinoma, mucoepidermoid carcinoma, and adenoidcystic carcinoma), pharynx cancers (e.g., squamous cell cancer, and verrucous), skin cancers (e.g., basal cell carcinoma, squamous cell carcinoma and melanoma, superficial spreading melanoma, nodular melanoma, lentigo malignant melanoma, acral lentiginous melanoma), kidney cancers (e.g., renal cell cancer, adenocarcinoma, hypernephroma, fibrosarcoma, transitional cell cancer (renal pelvis and/or uterer)), Wilms' tumor, bladder cancers (e.g., transitional cell carcinoma, squamous cell cancer, adenocarcinoma, carcinosarcoma), myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas, follicular lymphomas, carcinomas with p53 mutations, hormone dependent tumors of the breast, prostate and ovary, precancerous lesions such as familial adenomatous polyposis, and myelodysplastic syndromes.

Other specific diseases and disorders that may be treated by the methods provided herein include, but are not limited to, the following: allergic disorders, inflammation, asthma, arthritis, encephalitis, rheumatoid arthritis, osteoarthritis, psoriatic arthritis, inflammatory osteolysis, chronic or acute obstructive pulmonary disease, chronic or acute pulmonary inflammatory disease, inflammatory bowel disease, Crohn's Disease, gout, Bechet's Disease, Henoch-Schonlein purpura ("HSP"), septic shock, sepsis, meningitis, colitis, inflammation due to reperfusion, psoriasis, fibrosis including pulmonary fibrosis, Parkinson's disease, bradykinesia, muscle rigidity, Parkinsonian tremor, Parkinsonian gait, motion freezing, depression; defective long-term memory, Rubinstein-Taybi syndrome (RTS), dementia, sleep disorders, insomnia, postural instability, hypokinetic disorders, hyperkinetic disorders, synuclein disorders, multiple system atrophies, striatonigral degeneration, olivopontocerebellar atrophy, Shy-Drager syndrome, motor neuron disease with parkinsonian features, Lewy body dementia, Tau pathology disorders, progressive supraneulear palsy, corticobasal degeneration, frontotemporal dementia; amyloid pathology disorders, mild cognitive impairment, Alzheimer disease, Alzheimer disease with parkinsonism, Wilson disease, Hallervorden-Spatz disease, Chediak-Hagashi disease, SCA-3 spinocerebellar ataxia, X-linked dystonia parkinsonism, Huntington disease, prion disease, chorea, ballismus, dystonia tremors, Amyotrophic Lateral Sclerosis ("ALS"), CNS trauma, myoclonus, and diseases or disorders associated with undesired immune reaction (e.g., organ rejection associated with an organ transplant).

Viral infections that may be treated by the methods provided herein include, but are not limited to, the following: human immunodeficiency virus ("HIV"), herpes simplex virus type 1, herpes simplex virus type 2, influenza viruses, influenza virus type A, influenze virus type B, parainfluenza virus, human papillomavirus ("HPV"), adenoviruses, rhinoviruses, hepatitis A virus, hepatitis B virus, hepatitis C virus, hepatitis D virus, hepatitis E virus, dengue fever, yellow fever, West Nile virus, Japanese encephalitis virus, GB virus A, GB virus-B, GB virus-C, bovine viral diarrhea virus ("BVDV"), classical swine fever virus (i.e., hog cholera virus), border disease virus, varicella zoster virus, smallpox, measles, rabies virus, arbovirus, cytomegalovirus, mumps virus, poliovirus, coxsackie B virus, Epstein-Barr virus, rubella virus, parvovirus B19, coronaviruses (e.g., SARS coronavirus), astrovirus, norovirus, rotavirus, and adenoviruses.

Fungal infections that may be treated by the methods provided herein include, but are not limited to, aspergillosis, blastomycosis, coccidioidomycosis, cryptococcosis, fungal sinusitis, histoplasmosis, hypersensitivity pneumonitis, mucormycosis, paracoccidioidomycosis, sporotrichosis, and Valley Fever.

Bacterial infections that may be treated by the methods provided herein include, but are not limited to, brucellosis, cholera, leprocy, leptospirosis, shigellosis, trench fever, tularemia, Q fever, Whitmore's disease, yersiniosis, yaws, *vibrio vulnificus* infections, *streptococcus* infections, *staphylococcus* infections and *E. coli* infections.

EXAMPLES

Example 1

Preparation of Liposomes with No Drug: 6% L-α-Phosphatidylcholine (Soy) Liposome 6 g of L-α-phosphatidylcholine (Soy) was dispersed in 100 mL of water using a magnetic stirrer at 200 rpm for 10 minutes at ambient temperature. The dispersed liposome (multilayer) was passed through a Microtluidic homogenizer at 15,000 psi. Three cycles of passing resulted in a liposome less than 100 nm in diameter. Trehalose was then added to the liposome to a final concentration of 10% (w/w). The resulting stable isotonic liposome was either used as liquid or lyophilized.

Example 2

Preparation of Liposomes Encapsulated with Lapachone 200 mg of lapachone and 6 g of L-α-phosphatidylcholine (Soy) were dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in a liposome encapsulated with 2 mg/mL lapachone less than 100 nm in diameter. Trehalose was then added to the liposome to a final concentration of 10% (w/w). The resulting stable isotonic liposome encapsulated with lapachone was either used as liquid or lyophilized.

Example 3

Preparation of Liposomes Encapsulated and Micro Emulsified with Cyclosporine 500 mg of cyclosporine in 5 mL Mygliol and 6 g of L-α-phosphatidylcholine (Soy) were dispersed in 100 mL of water using a magnetic stirrer at 200 rpm for 10 minutes at ambient temperature. The dispersed liposome (multilayer) was passed through Microfluidic homogenizer at 15,000 psi. Three cycles of passing resulted in a liposome encapsulated with 5 mg/mL cyclosporine less than 100 nm in diameter. Trehalose was then added to the liposome to a final concentration of 10% (w/w). The resulting stable isotonic liposome formulation encapsulated and micro emulsified with cyclosporine was either used as liquid or lyophilized.

Example 4

Preparation of Liposomes Encapsulated with Transferrin 200 mg of transferrin and 6 g of L-α-phosphatidylcholine (Soy) were dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in a liposome encapsulated with 5 mg/mL transferrin less than 100 nm in diameter. Trehalose was then added to the liposome to a final concentration of 10% (w/w). The resulting stable isotonic liposome formulation encapsulated with transferrin was either used as liquid or lyophilized.

Example 5

Preparation of Liposomes Encapsulated with Colchicine 6 mg of sodium oleate, 10 g of trehalose and 6 g L-α-phosphatidylcholine (Soy) were dispersed in 100 mL of water using a magnetic stirrer at 200 rpm for 10 minutes at ambient temperature. The dispersed liposome (multilayer) was passed 10 times through a Microfluidic homogenizer at 15,000 psi. 100 μL of colchicine dissolved in acetone was spiked into 1 mL of the pre-made liposome and lyophilized. The resulting stable isotonic lyophilized liposome encapsulated with the drug is essentially free from organic solvent after lyophilization. After lyophilization, the product can be reconstituted as a 1 mg/mL, 2 mg/mL, 3 mg/mL or 4 mg/mL aqueous solution (e.g., Water For Injection).

All references cited herein are incorporated herein by reference in their entireties and for all purposes to the same extent as if each individual publication, patent or patent application was specifically and individually indicated to be incorporated by reference in its entirety for all purposes.

What is claimed is:

1. A method of preparing a pharmaceutical composition comprising unilamellar liposomes, wherein the unilamellar liposomes comprise a hydrophobic pharmaceutical agent, the method comprising:
   (a) forming a suspension of multilamellar liposomes by dispersing one or more solid phospholipids in an aqueous medium, wherein the aqueous medium is free of organic solvents and protein excipients, and the aqueous medium is at ambient temperature;
   (b) adding a disaccharide to the multilamellar liposome suspension, rendering the suspension isotonic;
   (c) homogenizing the multilamellar liposome suspension of step (b) to form an isotonic suspension of unilamellar liposomes;
   (d) adding the hydrophobic pharmaceutical agent as a solid to the isotonic suspension of unilamellar liposomes and subjecting the mixture to microfluidization to form the pharmaceutical composition comprising unilamellar liposomes, wherein the unilamellar liposomes are less than about 100 nm in diameter and comprise the hydrophobic pharmaceutical agent.

2. The method of claim 1, wherein the homogenizing is carried out with a microfluidic homogenizer.

3. The method of claim 1, wherein the one or more phospholipids comprise L-α-phosphatidylcholine.

4. The method of claim 1, wherein the disaccharide is trehalose.

5. The method of claim 4, wherein the trehalose concentration of the pharmaceutical composition is 10% by weight.

6. The method of claim 1, wherein the hydrophobic pharmaceutical agent is lapachone, colchicine, cyclosporine, transferrin, or a pharmaceutically acceptable salt thereof.

7. The method of claim 1, wherein the hydrophobic pharmaceutical agent is lapachone, or a pharmaceutically acceptable salt thereof.

8. The method of claim 1, wherein the hydrophobic pharmaceutical agent is colchicine, or a pharmaceutically acceptable salt thereof.

9. The method of claim 1, wherein the hydrophobic pharmaceutical agent is cyclosporine, or a pharmaceutically acceptable salt thereof.

10. The method of claim 1, wherein each of steps (a)-(d) is performed without the application of heat.

11. The method of claim 1, wherein the method is performed without the use of inorganic salts.

12. The method of claim 1, wherein the one or more solid phospholipids is soy phosphatidylcholine.

13. A method of preparing a pharmaceutical composition comprising unilamellar liposomes, wherein the liposomes comprise a hydrophobic pharmaceutical agent, the method comprising:
(a) forming liposomes by concurrently mixing one or more solid phospholipids, a disaccharide, and the hydrophobic pharmaceutical agent added as a separate component in solid form in an aqueous medium to produce multilamellar liposomes comprising the hydrophobic pharmaceutical agent, wherein the aqueous medium is free of organic solvents, surfactants, and protein excipients, and the aqueous medium is at ambient temperature; and
(b) homogenizing the composition of (a) to form the pharmaceutical composition comprising unilamellar liposomes, wherein the unilamellar liposomes are less than about 100 nm in diameter and comprise the hydrophobic pharmaceutical agent.

14. The method of claim 1, wherein the phospholipid is hydrogenated L-α-phosphatidylcholine.

15. The method of claim 13, wherein step (b) is performed without applying heat.

16. The method of claim 1, wherein the concentration of the hydrophobic pharmaceutical agent in the unilamellar liposomes is at least about 3.5 mg/mL.

17. The method of claim 1, wherein the concentration of the hydrophobic pharmaceutical agent in the unilamellar liposomes is about 5 mg/mL.

18. The method of claim 1, further comprising (e) homogenizing the pharmaceutical composition.

19. The method of claim 18, further comprising (f) lyophilizing the pharmaceutical composition.

20. The method of claim 1, wherein adding the hydrophobic active agent comprises adding more than one active agent to the dispersed unilamellar liposomes.

21. The method of claim 13, wherein the hydrophobic pharmaceutical agent is lapachone, colchicine, cyclosporin, transferrin, or a pharmaceutically acceptable salt thereof.

* * * * *